United States Patent
Hashimoto et al.

(10) Patent No.: US 8,409,271 B2
(45) Date of Patent: Apr. 2, 2013

(54) STENT HAVING A LOCKING PART WHICH PREVENTS THE STRUT FROM SLIDING OUT OF THE JUNCTION PIPE

(75) Inventors: Yasushi Hashimoto, Utsunomiya (JP); Masaaki Matsutani, Utsunomiya (JP); Masatoshi Fukuda, Utsunomiya (JP)

(73) Assignee: Mani, Inc., Tochigi (JP)

( * ) Notice: Subject to any disclaimer, the term of this patent is extended or adjusted under 35 U.S.C. 154(b) by 99 days.

(21) Appl. No.: 12/374,345

(22) PCT Filed: Jul. 6, 2007

(86) PCT No.: PCT/JP2007/063566
§ 371 (c)(1), (2), (4) Date: Jan. 19, 2009

(87) PCT Pub. No.: WO2008/013042
PCT Pub. Date: Jan. 31, 2008

(65) Prior Publication Data
US 2009/0326636 A1     Dec. 31, 2009

(30) Foreign Application Priority Data
Jul. 25, 2006   (JP) .................................. 2006-201918

(51) Int. Cl.
*A61F 2/06* (2006.01)
(52) U.S. Cl. ..................................................... 623/1.15
(58) Field of Classification Search .................. 606/198, 606/194; 623/1.11–1.16
See application file for complete search history.

(56) References Cited

U.S. PATENT DOCUMENTS

| | | | | |
|---|---|---|---|---|
| 2,037,856 A | * | 4/1936 | Filippi | 83/651.1 |
| 6,001,068 A | | 12/1999 | Uchino et al. | |
| 2005/0240257 A1 | * | 10/2005 | Ishimaru et al. | 623/1.15 |

FOREIGN PATENT DOCUMENTS

| | | |
|---|---|---|
| JP | 61-88935 A | 5/1986 |
| JP | 11-57014 A | 3/1999 |
| JP | 56-143135 A | 3/1999 |
| JP | 2001-304210 A | 10/2001 |
| JP | 2003-062087 A | 3/2003 |
| JP | 2004-097382 A | 4/2004 |
| JP | 2004-97382 A | 4/2004 |
| WO | WO 03097155 | * 11/2003 |

OTHER PUBLICATIONS

Supplementary European Search Report issued Mar. 1, 2010, in corresponding EP Application No. 07 76 8298.

* cited by examiner

*Primary Examiner* — Tuan V Nguyen
(74) *Attorney, Agent, or Firm* — Smith Patent Office

(57) ABSTRACT

A stent has a stent main wire. The strut is disposed adjacent to the stent main wire and a junction pipe disposed around the stent main wire and strut so as to affix the stent main wire to the strut. A locking part is formed at an end of the strut to prevent the strut from sliding out of the junction pipe. The locking part comprises a folded back portion, wherein a distal most end of the folded back portion abuts with a distal most end of the junction pipe, a swelling portion, wherein a distal most end of the swelling portion is abutting a distal most end of the junction pipe, or a bent portion, wherein a distal most end of the bent portion is abutting with a distal most end of the junction pipe.

1 Claim, 5 Drawing Sheets

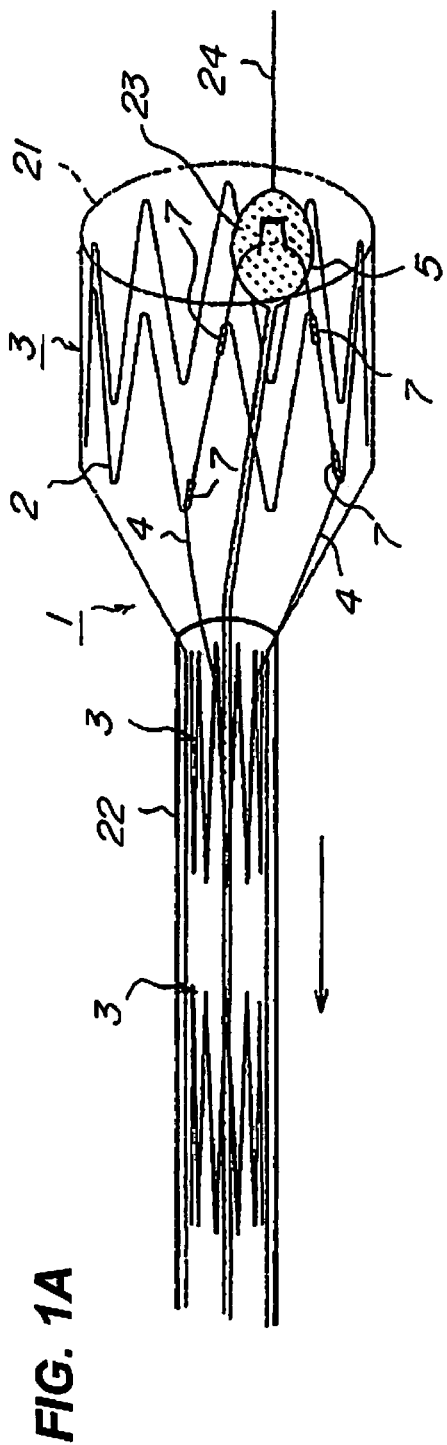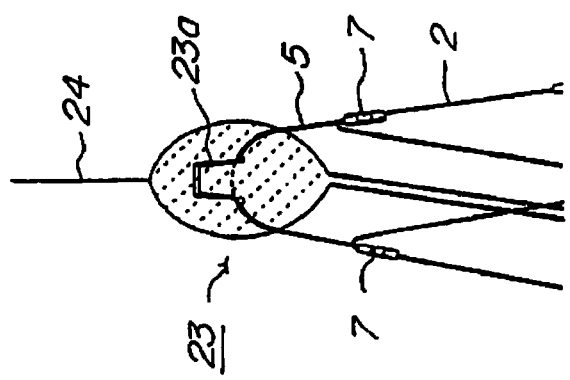

FIG. 4A
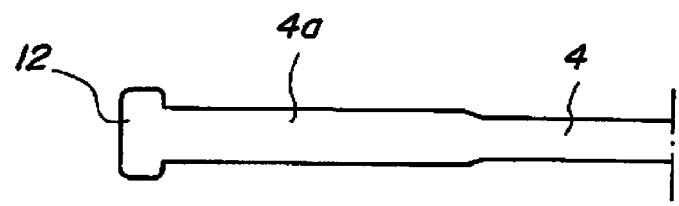
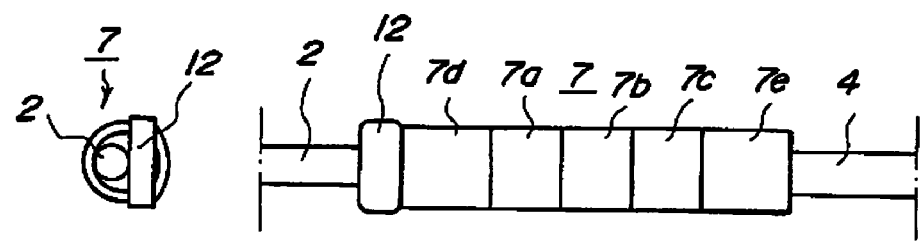
FIG. 4B
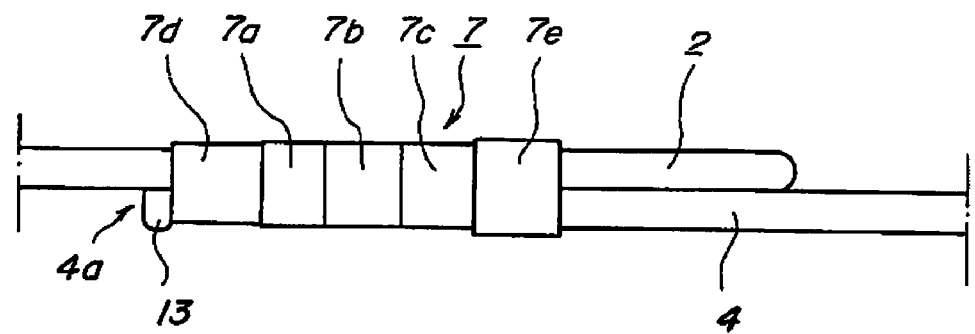

STENT HAVING A LOCKING PART WHICH PREVENTS THE STRUT FROM SLIDING OUT OF THE JUNCTION PIPE

CROSS REFERENCE TO RELATED APPLICATION

The present application is a national stage application of PCT Application No. PCT/JP2007/063566, filed Jul. 6, 2007, which claims priority of JP 2006-201918, filed Jul. 25, 2006.

TECHNICAL FIELD

The present invention relates to a stent used for medical treatment of a tubal tissue in a body such as a blood vessel, and more particularly, to a stent which is configured so that a stabilizer hook or strut connected to a stent main wire can maintain a stable connected state.

BACKGROUND ART

In a human body, there are many tubal tissues such as a blood vessel, a bile duct, an ureter and an esophagus, and there is a fear that peculiar disease such as stricture and occlusion is generated. In the case of the blood vessel for example, diseases such as stricture, occlusion, aneurysm and varix is generated in some cases. The aneurysm is such a serious disease that rupture causes major bleeding, and it is necessary to conduct medical treatment swiftly. Therefore, in order to conduct effective medical treatment, various tools have been developed.

Recently, when medical treatment for a stricture portion of a blood vessel or aneurysm is conducted, a metal cylindrical tool called a stent has been used in many cases. For example, when medical treatment is conducted for a stricture portion, the stent is accommodated in a sheath or a catheter (hereinafter, referred to as sheath) and this is transferred to an affected area, and after it reaches the affected area, the stent is separated from the sheath, the stent is increased in diameter by a balloon to enlarge the stricture portion and the stent indwells therein. When medical treatment for aneurysm is conducted, a stent graft in which a stent is covered with artificial blood vessel is allowed to indwell in the aneurysm, and the stent graft is applied against the pressure of blood so that pressure is not applied to the aneurysm.

As the stent, there are provided a mesh stent in which metal mesh cylinder is used, and a loop stent using a cylindrical loop as a whole formed by bending a round rod wire member in a zigzag manner and by joining ends of the wire member as described in Patent Documents 1 and 2.

Especially in the case of the loop stent, there are two cases, i.e., a case in which a loop stent is used alone in correspondence with an affected area where the stent is allowed to indwell, and a case in which a plurality of loop stents are disposed in a longitudinal direction in accordance with a curving state of an affected area, and these loop stents are connected to each other through a wire part called a strut.

A stabilizer hook is mounted on a loop stent located at a top of the stent. The stabilizer hook is utilized when the stent accommodated in a sheath indwells in an affected area. A wire part is disposed in one or some of loop stents constituting the stent. The wire part is used when the stent is inserted into the sheath, or when a position of the stent is adjusted or the stent is pulled back to the sheath when the stent indwells in an affected area.

The loop stent constituting the stent, the stabilizer hook mounted on the top portion, the strut which connects adjacent loop stents with each other, and the pulling-back member are made of metal round rod wire members. Connection parts are formed in connection regions between the loop stent and the stabilizer hook, between the loop stent and the strut, and between the loop stent and the pulling-back member.

The connection part which connects the round rod wire members in the stent is constituted in such a manner that the stent main wire at an object region in the loop stent is formed flat, ends of the strut, the stabilizer hook and the pulling-back member are formed flat, the formed regions are superposed on each other and inserted into a substantially rectangular pipe, and the pipe is caulked as described in Patent Documents 1 and 2.

The stent constituted in the above-described manner is reduced in diameter and inserted into the sheath and sent to an affected area, and when the stent reaches the affected area, the stent is separated from the sheath utilizing stabilizer hook and the stent is increased in diameter by itself or by a balloon. The stent whose diameter is increased in the affected area comes into contact with an inner wall surface of a blood vessel for example, and medical treatment for the blood vessel can be conducted.

Patent Document 1: Japanese Patent Application Laid-Open No. 2003-062087
Patent Document 2: Japanese Patent Application Laid-Open No. 2004-097382

DISCLOSURE OF THE INVENTION

Since it is necessary that a stent which indwells in an affected area maintains stable performance semi permanently, the present inventors conducted various tests. These tests were conducted under conditions severer than a condition when the stent indwells in an affected area.

When the stent indwells in an affected area during the test, and when the stent is fixed to an organ utilizing the stabilizer hook and the sheath is pulled out, slip is generated in some cases between the stent main wire and the stabilizer hook, between the stent main wire and the strut and between the stent main wire and the pulling-back member in the connection parts by a force in a tensile direction applied to the stent. As a result, it was found that there was a fear that the stabilizer hook, the strut or the pulling-back member is separated from the pipe constituting the connection part.

It is an object of the present invention to provide a stent having no fear that the stabilizer hook, the strut or the pulling-back member does not separate even when a force in a tensile direction is applied to the stent.

In order to solve the above problem, the present invention provides a stent having a connection part in which wire parts including a stent main wire, a strut and a stabilizer hook are connected to each other through a junction pipe, wherein a locking part which is locked to the junction pipe is formed on the wire part which is inserted into the junction pipe.

According to the stent of the present invention, in the connection part in which wire parts constituting the stent including the stent main wire, the strut and the stabilizer hook are connected to each other through the junction pipe, the wire part is formed with the locking part which is locked to the junction pipe. Therefore, when the stent is inserted into the sheath, or when the stent indwells in an affected area and the stent is separated from the sheath, a force in the tensile direction applied to the stent is applied to the connection part through the wire part, and even when attempt is made to generate slip between the wire parts, since the wire parts are locked to the junction pipe by the locking part, the wire parts do not separate from the junction pipe.

Therefore, even when a force in the tensile direction is applied to the stent, it is possible to reliably maintain the connection between the wire parts which constitute the stent, and it is possible to provide a stent having high reliability.

BRIEF DESCRIPTION OF THE DRAWINGS

FIG. 1 are diagrams for describing an example of a relation between a sheath and a stent including a plurality of loop stents connected to each other through a strut;

FIG. 4 are diagrams for describing a structure of a connection part of a stent according to a second embodiment.

EXPLANATION OF REFERENCE NUMERALS

Figure 2:
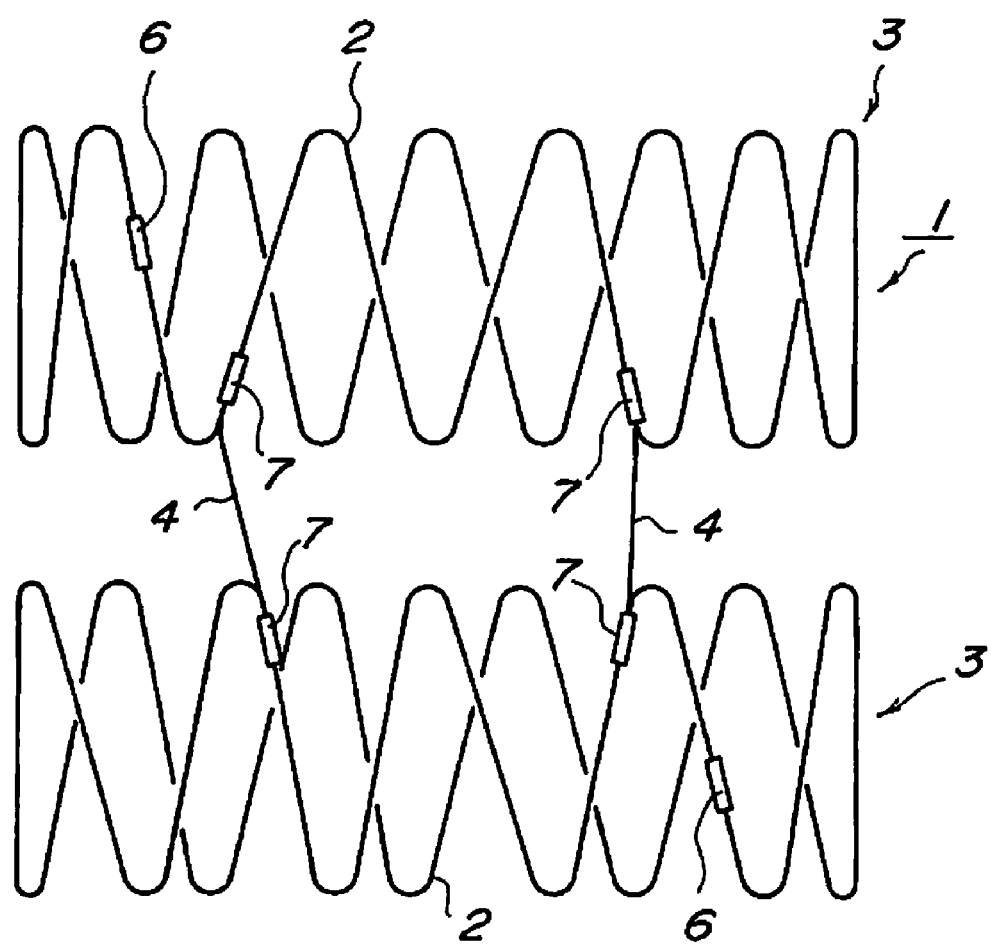
FIG. 2 is a diagram for describing a relation between the strut and the loop stent whose diameter is increased.

1: Stent
2: Stent main wire
3: Loop stent
4: Strut
4a: End
5: Stabilizer hook
6: Protection pipe
7: Junction pipe
7a to 7c: Unit pipe
7d, 7e: Auxiliary pipe
11: Folded-back portion
12: Swelling portion
13: Bent portion
14: Weld point
15: Cladding portion
21: Graft
22: Sheath
23: Dilator
23a: Notch
24: Guide wire

BEST MODE FOR CARRYING OUT THE INVENTION

Preferred embodiments of a stent according to the present invention will be described. A stent according to the present invention is applied to tubal tissue such as a blood vessel, a bile duct, an ureter and an esophagus in a human body. When disease such as stricture and occlusion is generated in these tubal tissues, especially in the case of the blood vessel, when aneurysm or varix is generated, the stent indwells in the affected area, and the stent has a function for reinforcing the tubal tissue in the affected area.

The stent of the invention includes a combination of the stent main wire and the strut made of metal round rod wire members, and wire parts such as the stabilizer hook. The connection parts of these wire parts are connected to each other through the junction pipe. That is, in the invention, the shape and the structure of the stent are not limited, but the invention is limited to the structure that the stent includes the wire parts, and the connection parts of the wire parts are connected to each other through the junction pipe.

Therefore, the stent need not to be of cylindrical shape, the stent may not be constituted as the loop stent, but the invention is limited to the structure that the cylindrical stent or the loop stent constituting the stent utilizes wire member. To avoid complication of explanation, a case in which the stent of the invention is constituted using a loop stent will be described.

The loop stent is formed into a cylindrical shape by bending a metal round rod wire member (stent main wire) in a zigzag form, butt welding both ends thereof or inserting the wire member into a sleeve and caulking the same. In the loop stent, both ends of the stent main wire are butt welded or caulked and non-rotatably connected to each other. Therefore, the diameter of the loop stent is not reduced and when the stent is inserted into the sheath, and the stent does not deform. Therefore, when the stent is separated from the sheath and the diameter of the stent is increased, the stent can precisely return to its original shape.

In the invention, the length and thickness of the stent are not limited, and the stent has appropriate shape and thickness in accordance with an affected area where the stent indwells. Therefore, in one case, the stent includes one loop stent, and in other case, the stent includes a plurality of loop stents connected with each other in the longitudinal direction. In any of the cases, the stabilizer hook is connected to a top of the stent, and the pulling-back member is connected to the rear end thereof. When a plurality of loops are connected with each other in the longitudinal direction, the loops are connected to each other through the strut.

In the stent of the invention, one loop stent and a stabilizer hook connected to the loop stent are absolutely necessary, but other parts such as the strut and the pulling-back member are not absolutely necessary. That is, the strut is necessary when the plurality of loop stents are connected to each other to constitute the stent, and when the stent includes one loop stent, the strut is not required.

As described above, the stent is not constituted only by the loop stent, the stabilizer hook, the strut and the pulling-back member, but includes a plurality of parts such as a ring and a fin used for covering an artificial blood vessel in addition to the members if required. These parts are constituted as wire parts using metal wire members having circular cross sections.

That is, in the invention, the wire part is necessary for constituting the stent and is made of metal, and the wire part is an object of all parts connected to the loop stent or the strut through the junction pipe. Therefore, in the following description, if a part which omitted constitutes the stent of the present invention, this part is included.

In the invention, material of the metal wire member constituting the wire part such as the loop stent and strut is not especially limited, and material having appropriate resilience and flexibility and which does not affect a living body tissue can be utilized. Examples of such metal are metal wire members of a stainless steel and a shape-memory alloy such as Ni—Ti alloys and these materials can selectively be used.

As material of the wire part is preferably austenitic stainless steel wire member having high reliability with respect to biocompatibility. A wire member obtained by extending tissues into fiber shape by cold wire drawing austenitic stainless steel wire member having a predetermined diameter with a preset reduction of area is preferable because such wire member maintains appropriate resilience and flexibility for a long term and has high toughness.

For example, in a connection part of a wire part including a loop stent and a strut, an end of the strut is superposed on a stent main wire constituting the loop stent, and the superposed portion is inserted into the junction pipe. The loop stent which is the wire part is connected to the loop stent which is the wire part by caulking the junction pipe.

In the invention, the shape of the junction pipe is not limited, and it is only necessary that a wire member in the connection part can be inserted into the junction pipe. In the invention, the cross section shape of the connection part of the wire member constituting the wire part is not limited. That is, the cross section shape of the wire member in the connection part may be circular, flat square or other shape. It is preferable that the shape is appropriately set in accordance with conditions required for the connection part, such as a condition which allows the connection part to relatively rotate or which does not allow the relative rotation.

Therefore, the connection part may be an elliptic pipe obtained by flattening a circle. Especially in order to prevent the relative rotation of the wire part, it is preferable that the connection region of the wire part is flattened, and the cross section of the junction pipe is angled so that the flattened wire part can be inserted into the junction pipe.

The length of the junction pipe is not limited only if the wire parts can reliably be connected to each other. Especially, when the stent is the loop stent, a step for connecting the wire part to the loop stent is carried out after the loop stent is produced. Therefore, the junction pipe is inserted into the stent main wire before the end surfaces of the loop stent are welded. That is, it is necessary that the junction pipe can smoothly pass through the zigzag bent portion formed with the loop stent.

Thus, the junction pipe includes one pipe in some cases, but it is preferable in some cases that the junction pipe includes a plurality of short unit pipes which can easily pass through the zigzag bent portion. Thus, the invention is not limited to the structure that the junction pipe includes one pipe, and the plurality of unit pipes may be continuously formed.

Material of the junction pipe is not especially limited only if the material does not affect the living body, and when the caulking force is applied, the material is deformed in accordance with this force, and the material can maintain the sufficient strength over long term. As a material constituting the junction pipe, it is preferable that a pipe made of austenitic stainless steel is used.

In the invention, the locking part locked to the junction pipe is formed on the wire part. With this, when the wire part is likely to be pulled from the junction pipe by a force applied to the strut or the loop stent which is the wire part, the locking part is locked to the junction pipe and the connected state is maintained.

It is not always necessary to form the locking parts formed on the wire parts on both the wire parts of the junction parts, but it is absolutely necessary that the wire part whose end is inserted into the junction pipe is formed with the locking part. That is, in order to prevent the wire part from separating from the junction pipe disposed on the connection part, the locking part is formed on the wire part having a fear that it separates from the junction pipe. Therefore, in the connection part between the loop stent and the strut, if the locking part is formed on the end which is to be inserted into the junction pipe of the strut, it is possible to prevent the connection part from separating from the junction pipe of the strut.

However, when the locking part is formed on the wire part whose end is inserted into the junction pipe, it is possible to prevent the wire part from separating from the junction pipe, but there is a fear that the junction pipe moves along the other wire part. For example, when the locking part is formed only on the strut in the connection part between the loop stent and the strut, there is a fear that the strut and the junction pipe move along the stent main wire of the loop stent by a force applied to the strut. To prevent such movement, it is preferable that the locking part is formed also on the loop stent.

It is not especially limited whether the locking parts are formed on both the wire parts or the locking part is formed on one of the wire parts, and it is preferable that it is appropriately set in accordance with a function of a wire part constituting the connection part.

The shape or the structure of the locking part formed on the wire part are not especially limited only if the locking part can be locked to the junction pipe when a force in the pulling-out direction is applied to the wire part from the junction pipe.

That is, as the locking part, there are a structure in which the shape of a portion of the wire member constituting the wire part is deformed and the deformed portion is locked to the junction pipe as a locking part, and a structure in which the junction pipe and the wire part inserted into the junction pipe are welded and locked. It is preferable to appropriately select a structure in accordance with a thickness of the wire member constituting the wire part and a magnitude of the applied force.

When a portion of the wire member constituting the wire part is deformed, a portion of the wire member protruding from the junction pipe is bent substantially at right angles, and this bent portion can be locked to the end of the junction pipe, and the portion of the wire member protruding from the junction pipe can be folded back 180° in the opposite direction and can be locked to the end of the junction pipe. The locking part having such a shape is preferable when the end of the wire member of the wire part in the connection part is inserted into the junction pipe.

It is also possible to press a portion of a wire member constituting a wire part separated away from an end of a junction pipe to form a swelling portion, and this swelling portion can be locked to the end of the junction pipe. Further, a portion which is inserted into the junction pipe is previously pressed into a wedge shape, and when the junction pipe is caulked, the wedge portion is engaged with the junction pipe and the wedge portion can be locked. The locking part having such a shape can be applied to any wire parts in the connection part.

As described above, when the locking part formed on the wire part deforms a portion of the wire member, it is preferable depending upon the magnitude of the deformation that a portion of the wire member corresponding to the locking part is previously annealed. Especially in the case of a wire member which is hardened or work hardened, there is a fear that the wire member may become cracked when the wire member is subjected to plastic working. Thus, if the wire member is softened by annealing, reliable working can be carried out.

Extremely thinned laser beam can be emitted from an outer peripheral side of a junction pipe into which a wire part is inserted and spot welding can be conducted as a locking part. In this case, if both wire parts inserted into the junction pipe and the junction pipe are welded to each other, the welded portion can function as the locking part.

As described above, it is not always necessary that the locking part is formed by deforming the shape of the wire part, and the locking part may have such a structure that the shape of the wire member is not varied such as welding and adhering.

The locking part formed on the wire part deforms a portion protruding from the junction pipe (folding or folding back of the wire member, or swelling portion caused by press), it is preferable to polish a sharp edge or burr so that they do not affect a balloon or an artificial blood vessel, and the folding portion or folded back end has substantially the same size as the outer diameter of the junction pipe.

(Embodiment 1)

Figure 3:
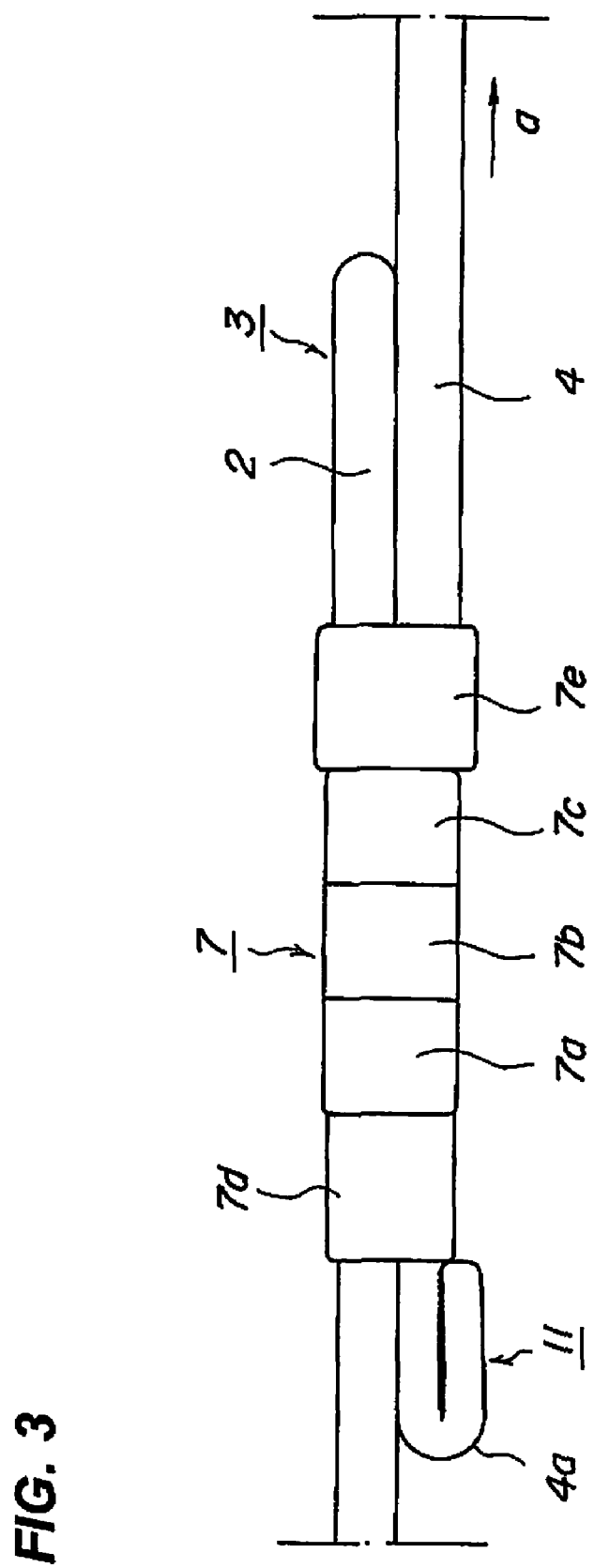
FIG. 3 is a diagram for describing a structure of a connection part.

Next, an embodiment of a stent according to the present invention will be described with reference to the drawings. FIG. 1 are diagrams for describing a relation between a sheath and a stent constituted by connecting a plurality of loop stents with each other through a strut. FIG. 2 is a diagram for describing a relation between the strut and the loop stent whose diameter is increased. FIG. 3 is a diagram for describing a structure of a connection part.

As shown in FIGS. 1 and 2, a stent 1 according to this embodiment is constituted as a complex stent in which a stent main wire 2 is bent in a zigzag form, end surfaces of a stent main wire 2 butted against each other and welded, thereby disposing a plurality of loop stents 3 formed into a loop in series, and these loop stents 3 are connected to each other through at least two struts 4. A stabilizer hook 5 is connected to one of the top loop stent 3.

At a butt welded portion of the stent main wire 2 of the loop stent 3 and a portion near the butt welded portion, austenitic tissue extending into a fiber form is thermally affected by welding and becomes coarse granular tissue, and its strength is deteriorated. Therefore, protection pipes 6 are disposed at the welded portion and near the welded portion, and the portion deteriorated by the welding is reinforced by the protection pipe 6.

Junction pipes 7 are disposed at a connection part between the loop stent 3 and the strut 4 and at a connection part between the loop stent 3 and the stabilizer hook 5. The strut 4 in which the junction pipe 7 is formed with the stent main wire 2 and a later-described locking part, or the stabilizer hook 5 is inserted into the junction pipe 7 and they are integrally connected to each other by caulking, and the locking part is locked to the junction pipe 7.

The stent main wire 2 constituting the loop stent 3 is made of such material that a wire member made of SUS316L which is preferably utilized as austenitic stainless steel, particularly implant stainless is cold wire drawn and tissue is extended into fiber form, working hardening effect can be exhibited and mechanical properties are enhanced. According to the loop stent 3 made of such material, compatibility with respect to a living body is excellent and appropriate expansion force is exhibited. Therefore, when the loop stent 3 reaches a target affected area and is separated from the sheath, the loop stent 3 returns to its original shape and can reinforce the affected area for a long term.

The strut 4 and the stabilizer hook 5 are also made of austenitic stainless steel wire member which is the same as the stent main wire 2, especially material in which tissue is extended into fiber form by cold wire drawing a wire member made of SUS316L.

Thicknesses of the loop stent 3, the strut 4 and the stabilizer hook 5 constituting the wire member are varied depending upon organs in which the stent indwells, but a diameter of the stent main wire of the loop stent 3 is about 0.4 to 0.5 mm, and diameters of the strut 4 and the stabilizer hook 5 are about 0.5 mm in this example.

Pipes made of SUS316L which is preferably utilized as implant stainless like the stent main wire 2 are used as the protection pipe 6 and the junction pipe 7. Since the protection pipe 6 and the junction pipe 7 are caulked, it is unnecessary to harden them before they are used.

The protection pipe 6 is inserted into the stent main wire 2 immediately before the zigzag shaped stent main wire 2 is butt-welded. Thus, the protection pipe 6 is constituted as one pipe having sufficient length for protecting the welded portion.

After the stent main wire 2 is formed into zigzag shape, the junction pipe 7 is inserted into the stent main wire 2 before an end thereof is welded. Thus, it is necessary that the junction pipe 7 has such a length that the junction pipe 7 can easily pass through the smallest radius portion (zigzag bent portion) of the zigzag shaped stent main wire 2, and a plurality of short unit pipes are continuously connected as the junction pipe 7. When a diameter of the stent main wire 2 is 0.45 mm, the length of the unit pipe constituting the junction pipe 7 is set to 0.98 mm, and three unit pipes are continuously connected to constitute the junction pipe 6.

Next, a structure of the connection part in the stent 1 will be described with reference to FIG. 3. A connection part in the stent 1 between the loop stent 3 and the strut 4, a connection part between the loop stent 3 and the connection region of the stabilizer hook 5 and a connection part between other wire parts are formed. These connection parts have the same structures and thus, the structure of the connection part between the strut 4 and the stent main wire 2 of the loop stent 3 will be described as a representative.

The connection part of the stent 1 according to this embodiment is constituted by inserting the strut 4 and the stent main wire 2 of the loop stent 3 into the junction pipe 7 and by caulking them. The locking part is constituted by a folded-back portion 11 formed on an end 4a of the strut 4 protruding from the junction pipe 7.

The stent main wire 2 and the strut 4 are constituted utilizing wire members in which wires made of SUS316L are subjected to cold wire drawing and tissues are extended into fiber form. The junction pipe 7 is also constituted utilizing a pipe made of SUS316L.

The junction pipe 7 includes three unit pipes 7a to 7c having the same size and same material, and two auxiliary pipes 7d and 7e disposed on both sides of the unit pipes 7a to 7c in the longitudinal direction. The pipes 7a to 7e are previously inserted into the stent main wire 2 of the loop stent 3, and moved to a position where the pipes become the connection parts which connect the strut 4 along the stent main wire 2.

A predetermined length of the end 4a of the strut 4 is previously softened by annealing, the end 4a is inserted into the junction pipe 7 along the stent main wire 2, the end projects from the junction pipe 7, the end 4a is folded back 180° and the folded-back portion 11 is formed. The locking part is constituted by the folded-back portion 11. The strut 4 formed with the folded-back portion 11 is connected to the stent main wire 2 by caulking the junction pipe 7.

That is, the connection part of the stent 1 according to this embodiment is formed such that the junction pipe 7 which is previously inserted into the stent main wire is moved to a position where the strut 4 is to be connected, the end 4a is annealed to the junction pipe 7, and the end 4a is inserted into the strut 4 and projected therefrom. The end 4a of the strut 4 projecting from the junction pipe 7 is folded back 180° to form the folded-back portion 11 and then, a position of the strut 4 with respect to the stent main wire 2 is adjusted.

After the position of the strut 4 with respect to the stent main wire 2 (position of the strut 4 with respect to the loop stent 3) is adjusted, the strut 4 is pulled in a direction of the arrow a, and the folded-back portion 11 is engaged with an end surface of the junction pipe 7. In this state, the unit pipes 7a to 7c constituting the junction pipe 7 are strongly caulked, and the auxiliary pipes 7d and 7e are caulked or crushed.

As described above, the strut 4 can be connected to the stent main wire 2 of the loop stent 3 utilizing the junction pipe 7. According to the connection part having such a structure, the end surface of the strut 7 constituting the folded-back portion 11 is chamfered. A step formed between the stent main wire 2 and the junction pipe 7 becomes as small as possible so that the folded-back portion 11 does not damage a balloon when the diameter of the stent graft is increased.

It is not always form the folded-back portion 11 before it is caulked by the junction pipe 7, and after the strut 4 is inserted into the junction pipe 7 and the end 4a projects, the junction pipe 7 may be caulked and then, the end 4a is folded back 180° and the folded-back portion 11 may be formed.

A cross section of the loop stent 3 connected to the strut 4 in the stent main wire 2 and a cross section of the strut 4 inserted into the junction pipe 7 and caulked may have the original circular shapes, or may have flat shapes.

In the stent 1 having such a connection part, a force in the direction of the arrow a in FIG. 3 is applied to the strut 4, and even if the strut 4 tries to slip in the direction of the arrow a by this force, since the folded-back portion 11 abuts against and is locked to the end surface of the junction pipe 7, the strut 4 is not separated from the junction pipe 7.

In the junction pipe 7, the strut 4 and the stent main wire 2 which constitutes the loop stent 3 mainly by the unit pipes 7a to 7c are connected with each other, and the auxiliary pipes 7d and 7e prevent the strut 4 from being bent at an acute angle with respect to the stent main wire 2.

Next, procedure for connecting the plurality of loop stents 3 with each other through the strut 4 and indwelling the stent 1 to which the stabilizer hook 5 is connected in an affected area will be briefly described with reference to FIG. 1.

The stent 1 is formed with a cylindrical graft 21. A diameter of the graft 21 is reduced in accordance with an inner diameter of the sheath 22 and the graft 21 is accommodated in the sheath 22. A dilator 23 is accommodated in the sheath 22, and a guide wire 24 whose tip end is exposed to outside is accommodated in the sheath 22. The stabilizer hook 5 provided on the top of the stent 1 is caught in a notch 23a formed in the dilator 23.

A doctor operates an operation section located on hand, fixes the stabilizer hook 5 to an organ by the dilator 23 and in this state, the doctor pulls the sheath 22 to himself, the stabilizer is pulled out from the sheath 22 and a diameter of the stabilizer is increased, it indwells in the affected area, and medical treatment of the affected area can be conducted.
(Embodiment 2)

Next, another embodiment of the locking part formed on the strut 4 in the connection part constituted in the stent 1 will be described with reference to FIG. 4. In the stent of the invention, a structure thereof (structures of the loop stent 3 and the strut 4) other than the shape and structure of the locking part in the connection part is the same. Therefore, the structure of the connection part will be described.

In FIG. 4(a), a swelling portion 12 is formed on the end 4a of the strut 4, and the swelling portion 12 constitutes the locking part. The swelling portion 12 can be formed by presswork. If a diameter of the junction pipe 7 is selected, the junction pipe 7 can be formed before the strut 4 is inserted into the junction pipe 7.

When the locking part including the swelling portion 12 is formed on the end 4a of the strut 4, the swelling portion 12 abuts against the end surface of the junction pipe 7 and is locked to the end surface, and even when a force in the pulling direction from the junction pipe 7 is applied to the strut 4, the strut 4 does not separate.

FIG. 4(b) shows that the end 4a of the strut 4 is bent substantially at right angles to form a bent portion 13, and the bent portion 13 constitutes the locking part. The bent portion 13 may be formed before the strut 4 is inserted into the junction pipe 7, or may be formed after the strut 4 is inserted into the junction pipe 7 and the junction pipe 7 is caulked.

In this manner, when the locking part including the bent portion 13 is formed on the end 4a of the strut 4, the bent portion 13 abuts against the end surface of the junction pipe 7 and is locked to the end surface, and even when a force in the pulling direction from the junction pipe 7 is applied to the strut 4, the strut 4 does not separate.

The folded-back portion 11 in the first embodiment, and the swelling portion 12 and the bent portion 13 in the second embodiment as described above constitute the locking part by varying the shape of the end 4a of the strut 4. When the shape of the end 4a of the strut 4 is varied to constitute the locking part in this manner, the shape of the locking part is not limited to the above-described shape, and any shape can be employed only if it is possible to maintain the function as the locking part that when a force in the pulling direction from the junction pipe 7 is applied to the strut 4, the strut 4 is locked to the junction pipe 7 in accordance with this force.

Therefore, a wedge may be inserted into a space formed between the stent main wire 2 of the loop stent 3, the strut 4 and the inner surface of the junction pipe 7 as the locking part, or the end of the strut 4 may be cut using a cutter to form a fin-like projection.
(Embodiment 3)

Next, another embodiment of the locking part formed on the strut 4 in the connection part constituted in the stent 1 will be described with reference to FIG. 5. In the stent 1 of this embodiment, a structure of the locking part is different from those of the previous embodiments, and the shape of the strut 4 is not varied.

Figure 5A:
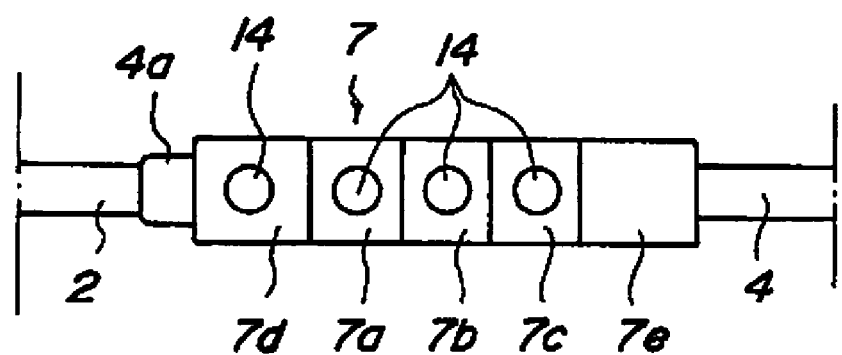
FIG. 5 are diagrams for describing a structure of a connection part of a stent according to a third embodiment.

FIG. 5(a) shows that the junction pipe 7 is inserted into the stent main wire 2 constituting the loop stent 3, the strut 4 is inserted into the junction pipe 7 and they are caulked. Then, the junction pipe 7 and the strut 4 are welded to each other, and this weld point 14 functions as the locking part.

The junction pipe 7 and the strut 4 may be welded by spot welding or laser welding, and any of which can preferably be utilized. When such a welding method is employed, the weld point 14 passing through the junction pipe 7, the strut 4 and the stent main wire 2 can be formed by selecting the welding direction, or a weld point 14 passing through the junction pipe 7 and the strut 4 can be formed.

In this manner, when the strut 4 and the junction pipe 7 are welded to each other and the locking part including the weld point 14 is formed, the weld point 14 is integrally locked to the junction pipe 7, and even when a force in the pulling direction from the junction pipe 7 is applied to the strut 4, the strut 4 does not separate.

Figure 5B:
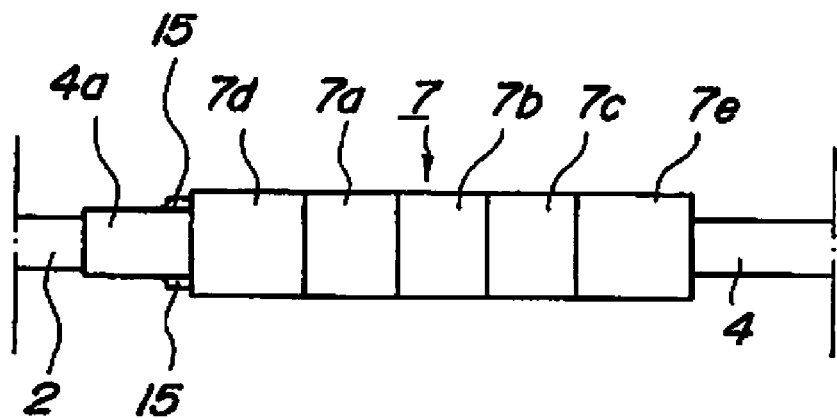

FIG. 5(b) shows a structure that a cladding portion 15 is formed on the end 4a of the strut 4 inserted into the junction pipe 7 projecting from the junction pipe 7 by laser welding or laser flame spraying, and the cladding portion 15 constitutes the locking part.

When the locking part including the cladding portion 15 is formed on the end 4a of the strut 4 in this manner, the cladding portion 15 abuts against the end surface of the junction pipe 7 and is locked to the junction pipe 7, and even when a force in the pulling direction from the junction pipe 7 is applied to the strut 4, the strut 4 does not separate.

According to the above-described third embodiment, the locking part in the connection part is formed by integrally welding the strut 4 and the junction pipe 7, or by forming the cladding portion by welding without deforming the strut 4 itself. With this structure also, when a force in the pulling-out direction from the junction pipe 7 is applied to the strut 4, the strut 4 can be locked to the junction pipe 7 in accordance with this force.

In each of the above embodiments, the locking part is formed on the end 4a of the strut 4, but the locking part may be formed on the stent main wire 2 of the loop stent 3 if necessary of course.

When the locking parts are formed on both of the stent main wire 2 and the strut 4, the connection part between the loop stent 3 and the strut 4 is not deviated in position, and the shape of the stent 1 can stably be maintained.

Industrial Applicability

When the stent 1 according to the present invention indwells in an affected area, even if a force is applied to the connection part when the stent 1 is pulled out from the sheath 22, there is no fear that the strut 4 separates from the junction pipe 7 by this force. Therefore, when the stent indwells in a human body for a long term, it is possible to exhibit high reliability.

The invention claimed is:

1. A stent comprising:
a stent main wire;
a strut disposed adjacent to the stent main wire; and
a junction pipe disposed around the stent main wire and strut so as to affix the stent main wire to the strut,
wherein a locking part is formed at an end of the strut to prevent the strut from sliding out of the junction pipe, said locking part comprised of a folded back portion, wherein a distal most end of the folded back portion is abutting with a distal most end of the junction pipe, a swelling portion, wherein a distal most end of the swelling portion is abutting a distal most end of the junction pipe, or a bent portion, wherein a distal most end of the bent portion is abutting with a distal most end of the junction pipe.

* * * * *